(12) United States Patent
Tabor (10) Patent No.: US 8,764,188 B2
(45) Date of Patent: Jul. 1, 2014

(54) FUNCTIONAL VISION TESTER

(71) Applicant: Kent Tabor, Pewaukee, WI (US)

(72) Inventor: Kent Tabor, Pewaukee, WI (US)

(*) Notice: Subject to any disclaimer, the term of this patent is extended or adjusted under 35 U.S.C. 154(b) by 15 days.

(21) Appl. No.: 13/657,570

(22) Filed: Oct. 22, 2012

(65) Prior Publication Data

US 2013/0100401 A1  Apr. 25, 2013

Related U.S. Application Data

(60) Provisional application No. 61/549,850, filed on Oct. 21, 2011.

(51) Int. Cl.
*A61B 3/08* (2006.01)
*A61B 3/00* (2006.01)
*A61B 3/02* (2006.01)

(52) U.S. Cl.
USPC .......................... 351/201; 351/245; 351/239

(58) Field of Classification Search
USPC .................................................. 351/200–246
See application file for complete search history.

(56) References Cited

U.S. PATENT DOCUMENTS

| | | | |
|---|---|---|---|
| 4,850,687 A | 7/1989 | Reis et al. | |
| 4,884,884 A | 12/1989 | Reis | |
| 4,907,872 A | 3/1990 | Schirmer et al. | |
| 4,976,535 A | 12/1990 | Reis | |
| 5,002,386 A | 3/1991 | Reis et al. | |
| 5,396,302 A | 3/1995 | Triller et al. | |
| 5,663,781 A | 9/1997 | Wilms et al. | |
| 5,760,872 A | 6/1998 | Reis et al. | |
| 5,895,384 A | 4/1999 | Steiner et al. | |
| 6,267,756 B1 | 7/2001 | Feuerstein et al. | |
| 6,299,310 B1 | 10/2001 | Reis | |
| 8,579,440 B2 * | 11/2013 | Feiertag et al. | 351/237 |
| 2006/0241970 A1 * | 10/2006 | Winiarski | 705/2 |
| 2006/0244915 A1 * | 11/2006 | Clemons et al. | 351/245 |
| 2011/0205491 A1 | 8/2011 | Koiwa et al. | |

FOREIGN PATENT DOCUMENTS

| | | |
|---|---|---|
| EP | 0487073 A1 | 5/1992 |
| EP | 0578236 A1 | 1/1994 |
| JP | 2010017279 A | 1/2010 |
| WO | 90/03759 A1 | 4/1990 |
| WO | 9409696 A1 | 5/1994 |

* cited by examiner

*Primary Examiner* — Mohammed Hasan
(74) *Attorney, Agent, or Firm* — Michael Best & Friedrich LLP (57) ABSTRACT

A vision testing device includes a partition defining a first side and a second side and an electronic device operable to project a first image to the first side and a second image to the second side. The first image and the second image comprise computer-generated images, and the first image is identical to but offset from the second image. A mirror extends from the first side to the second side and is positioned to reflect the first image and the second image. A first viewing lens is in optical communication with the first side and configured to receive the first image reflected from the mirror. A second viewing lens is in optical communication with the second side and configured to receive the second image reflected from the mirror.

33 Claims, 9 Drawing Sheets

FUNCTIONAL VISION TESTER

RELATED APPLICATION DATA

The present application claims priority under 35 U.S.C. §119 to Provisional Patent Application No. 61/549,850, filed Oct. 21, 2011, the entire contents of which is hereby incorporated by reference.

BACKGROUND

The present invention relates to a testing device for evaluating an individual's functional vision. Testing for functional vision includes tests done under day, night, and "glare" conditions at near, intermediate, and far distances. Testing can include, but is not limited to, acuities, phorias, stereopsis, color, contrast sensitivity, and peripheral assessment, using a multitude of optotypes and images.

Many of the tests are based on multiple visual effects perceived by the eyes. While many of these effects can be ascertained with one eye alone (e.g., relative size disparity, perspective view, and shading), stereopsis, for example, is an appreciation of depth based on the lateral displacement between both eyes. This lateral displacement produces two slightly offset views which, when evaluated by the brain, form a three dimensional image. Stereopsis is typically determined with vision testing equipment.

SUMMARY

More sophisticated testing equipment involves the use of an enclosure through which a user concurrently views two displaced images separated by a partition that isolates the right eye field of vision from the left eye field of vision. The displaced images are typically provided on slide plates that are illuminated from below. These slide plates are susceptible to damage and wear and must be switched or altered as necessary to accommodate the specific purpose of testing. Fluctuations in illumination quality over time can also affect the images perceived by the user and consequently the results obtained by the test. The images provided for such testing should be easily adjustable and of consistent quality while requiring minimum activity on the part of the equipment operator.

One embodiment of a vision testing device includes a partition defining a first side and a second side and an electronic device operable to project a first image to the first side and a second image to the second side. The first image and the second image comprise computer-generated images, and the first image is identical to but offset from the second image. A mirror extends from the first side to the second side and is positioned to reflect the first image and the second image. A first viewing lens is in optical communication with the first side and configured to receive the first image reflected from the mirror. A second viewing lens is in optical communication with the second side and configured to receive the second image reflected from the mirror.

Another embodiment of a vision testing device includes a partition defining a first side and a second side and an electronic device operable to project a first image to the first side and a second image to the second side. The first image and the second image comprise computer-generated images. A first viewing lens is configured to receive the projected first image and a second viewing lens is configured to receive the projected second image.

Another embodiment of a vision testing device includes an outer hood enclosing an internal space. The internal space includes an electronic device operable to project a computer-generated first image and a computer-generated second image. The second image is offset from the first image. A partition is disposed to separate the first image from the second image. A viewing member is coupled to the outer hood for providing viewing access to the internal space. The viewing member includes a first viewing lens configured to receive the first image and a second viewing lens configured to receive the second image.

In yet another embodiment, the invention provides a method of testing the vision of a test subject using a single vision testing apparatus. The method includes providing a subject viewing space including a first pair of view windows and a second pair of view windows and projecting a first image using an image projecting system. The first image is arranged to be viewed by the left eye of the test subject. The method also includes projecting a second image using the image projecting system. The second image is arranged to be viewed by the right eye of the test subject and is at least one of different than the first image and identical but offset from the first image. The method further includes separating the first image and the second image such that the first image is not viewable by the right eye at the same time that the second image is viewed by the left eye.

In another embodiment, the invention provides a vision testing system autonomously operable to evaluate the vision of a plurality of different test subjects having different backgrounds. The vision testing system includes a computer including a database of vision tests, each vision test having a pass/fail criteria based at least in part on the background of the test subject. A monitor is coupled to the computer and is operable in response to the computer to display a left side image and a right side image. A divider is positioned to separate the left side image and the right side image. A first viewing station includes a first viewing port arranged to selectively provide a view of the left side image and the right side image and a second viewing port arranged to selectively provide a view of the left side image and the right side image. A first optics path is positioned to direct the left side image and the right side image to the first viewing port. The first optics path is arranged to simulate a near field view of the left side image and the right side image. A second optics path is different than the first optics positioned to direct the left side image and the right side image to the second viewing port. The second optics path is arranged to simulate a far field view of the left side image and the right side image.

In still another embodiment, the invention provides a vision testing system operable to perform a plurality of optical tests. The vision testing system includes a video image producing device operable to produce a left side image and a right side image, a mechanical divider positioned to separate the left side image and the right side image, and a first optics path positioned to direct the left side image and the right side image to the first viewing port. The first optics path is arranged to simulate a near field view of the left side image and the right side image. A second optics path, different than the first optics path is arranged to simulate a far field view of the left side image and the right side image. A computer is operable to select an optical standard to be tested against from a plurality of stored standards. The computer is also operable to select the right side image and the left side image based on the optical test being performed and the standard being tested and to compare the test results to the selected standard for the selected optical test to determine if the test subject passes or fails the test.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. And as used herein and in the appended claims, the terms "upper", "lower", "top", "bottom", "front", "back", and other directional terms are not intended to require any particular orientation, but are instead used for purposes of description only.

Figure 1:
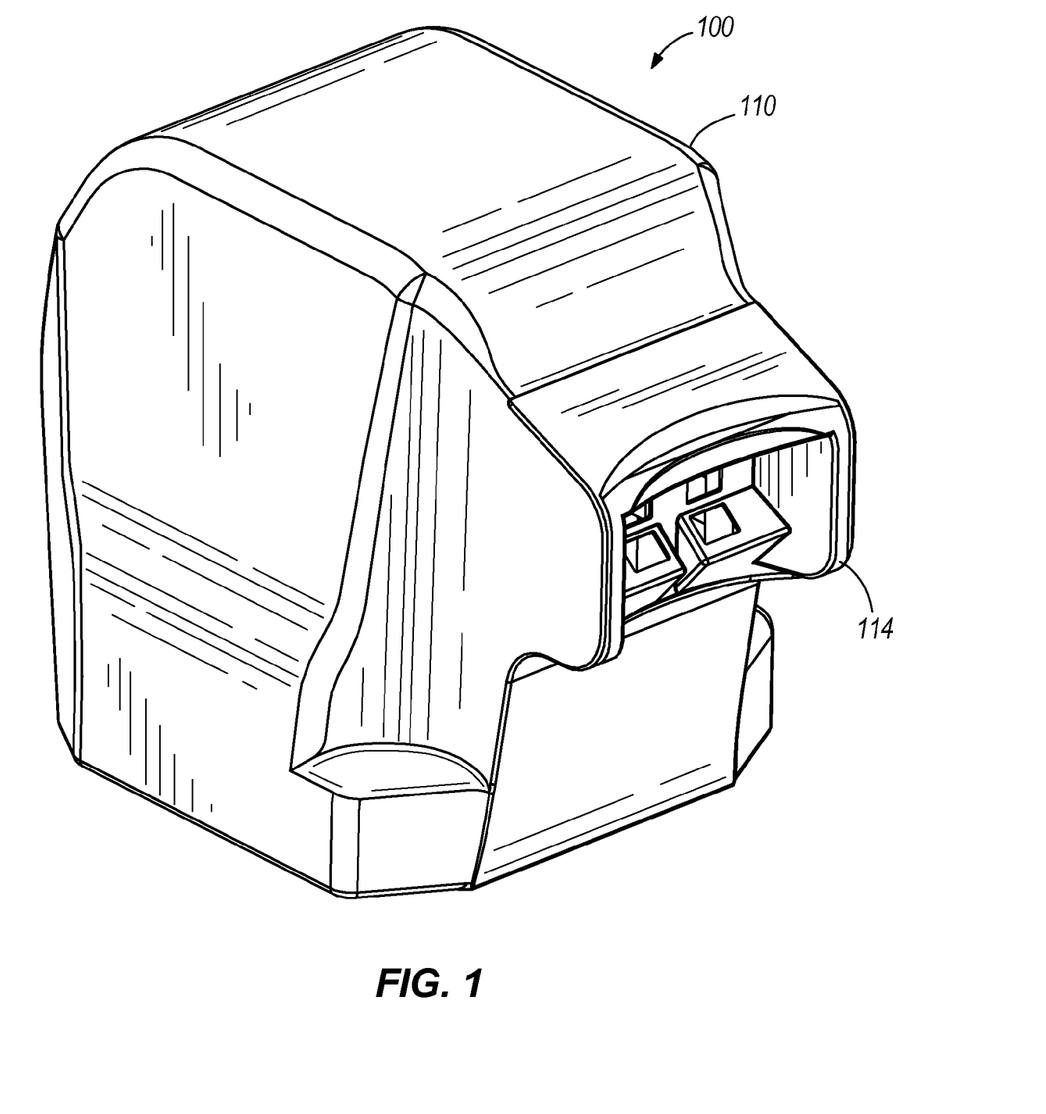
FIG. 1 is an external perspective view of a vision tester that can perform numerous vision tests, including but not limited to, stereopsis testing.
Figure 2:
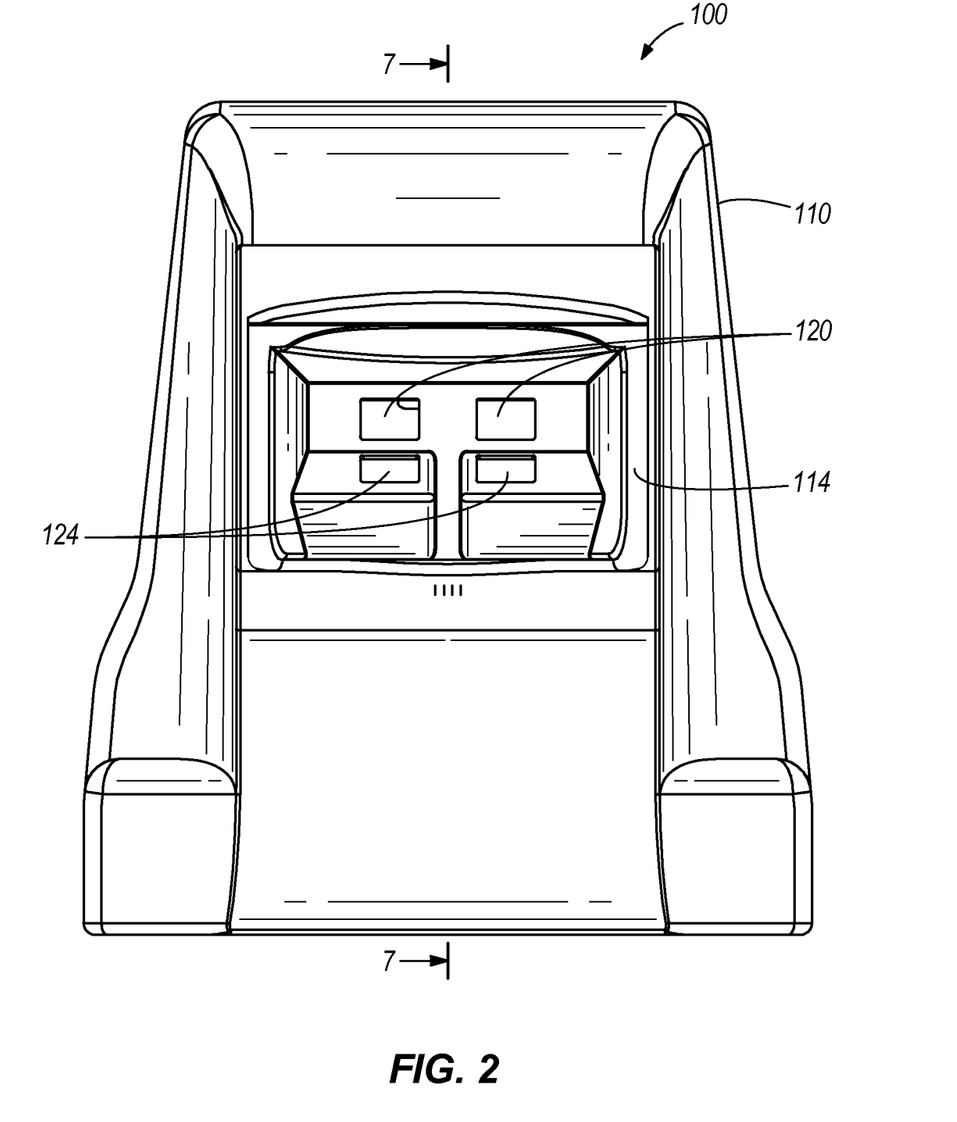
FIG. 2 is front view of the vision tester of FIG. 1.

FIGS. 1 and 2 illustrate an external view of a vision tester 100 for testing the vision of a test subject including, but not limited to, stereoscopic depth perception of the test subject. An outer hood 110 encloses the internal components of the tester and an optics head 114 provides viewing access to testing images produced within. The optics head 114 includes two sets of viewing lenses. A far field lens set 120 is used for evaluating far field vision, while a near field lens set 124 is used for evaluating near field vision. The near field set 124 is positioned at an angle relative to the far field set 120, as will be further explained below. The outer hood 110 and optics head 114 are primarily plastic (e.g., polycarbonate resin), but in other embodiments could be of any suitable materials.

Figure 3:
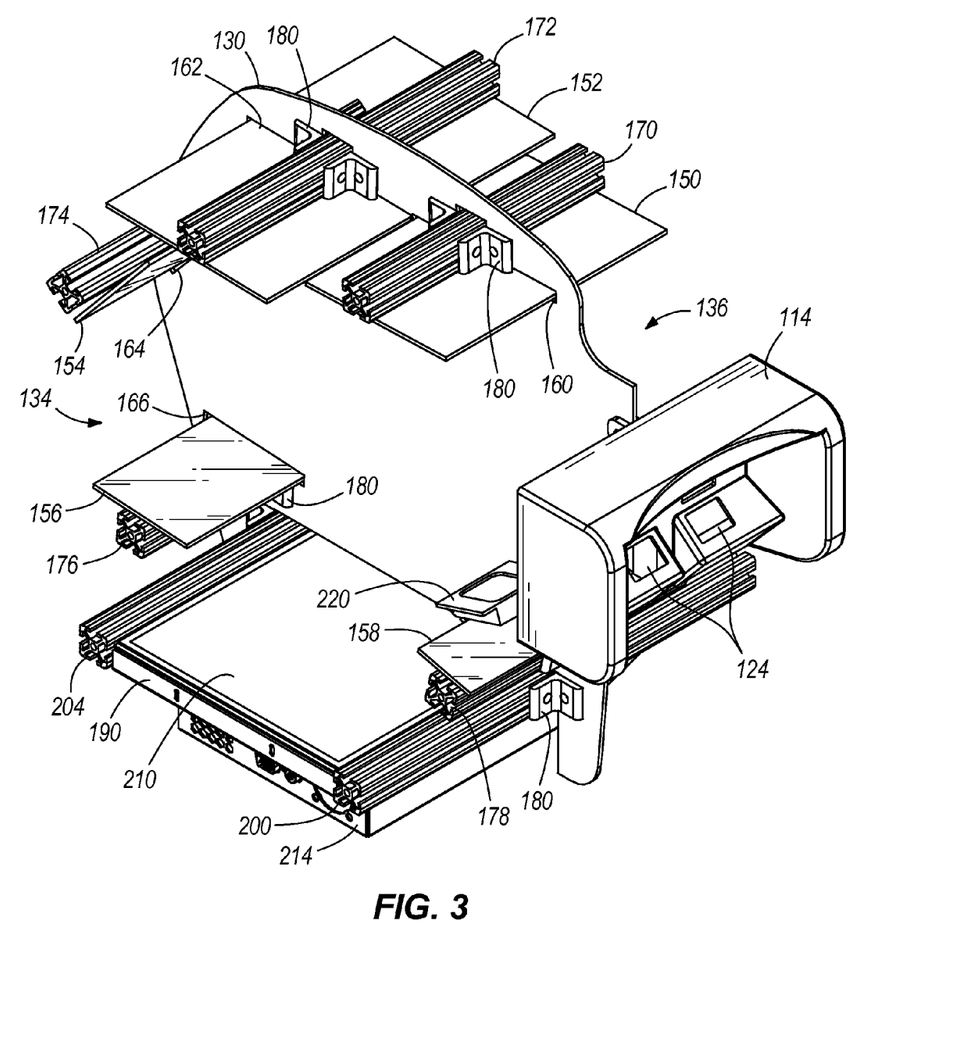
FIG. 3 is an internal perspective view of the vision tester of FIG. 1.
Figure 4:
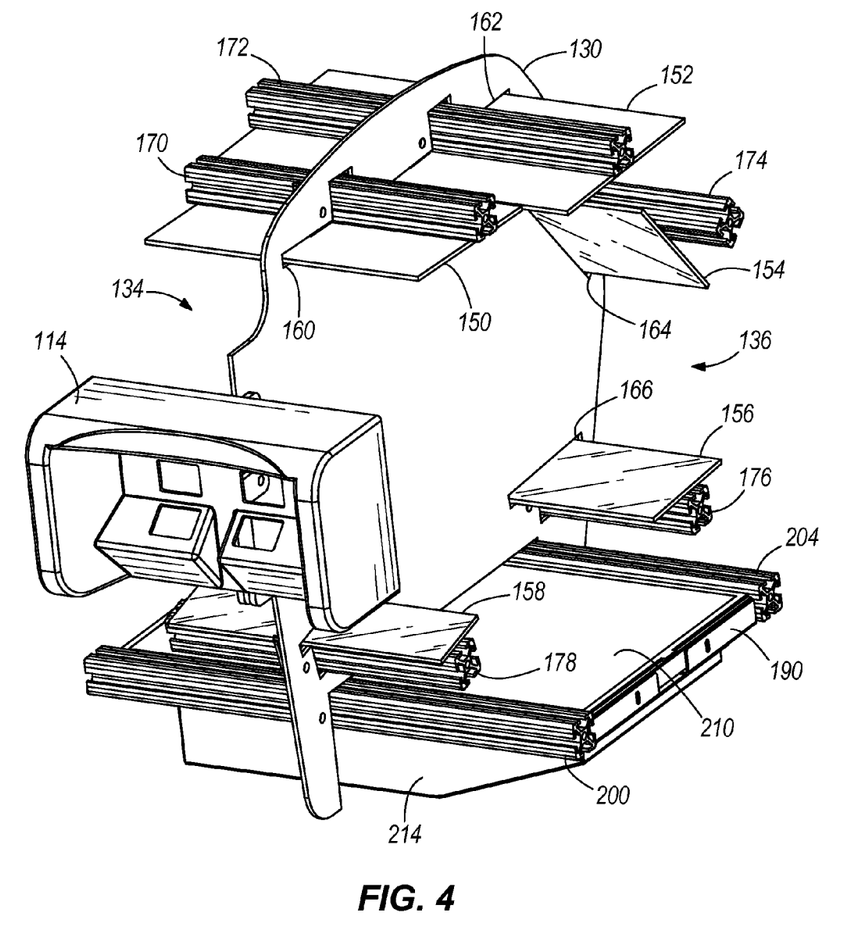
FIG. 4 is a second internal perspective view of the vision tester of FIG. 1.
Figure 5:
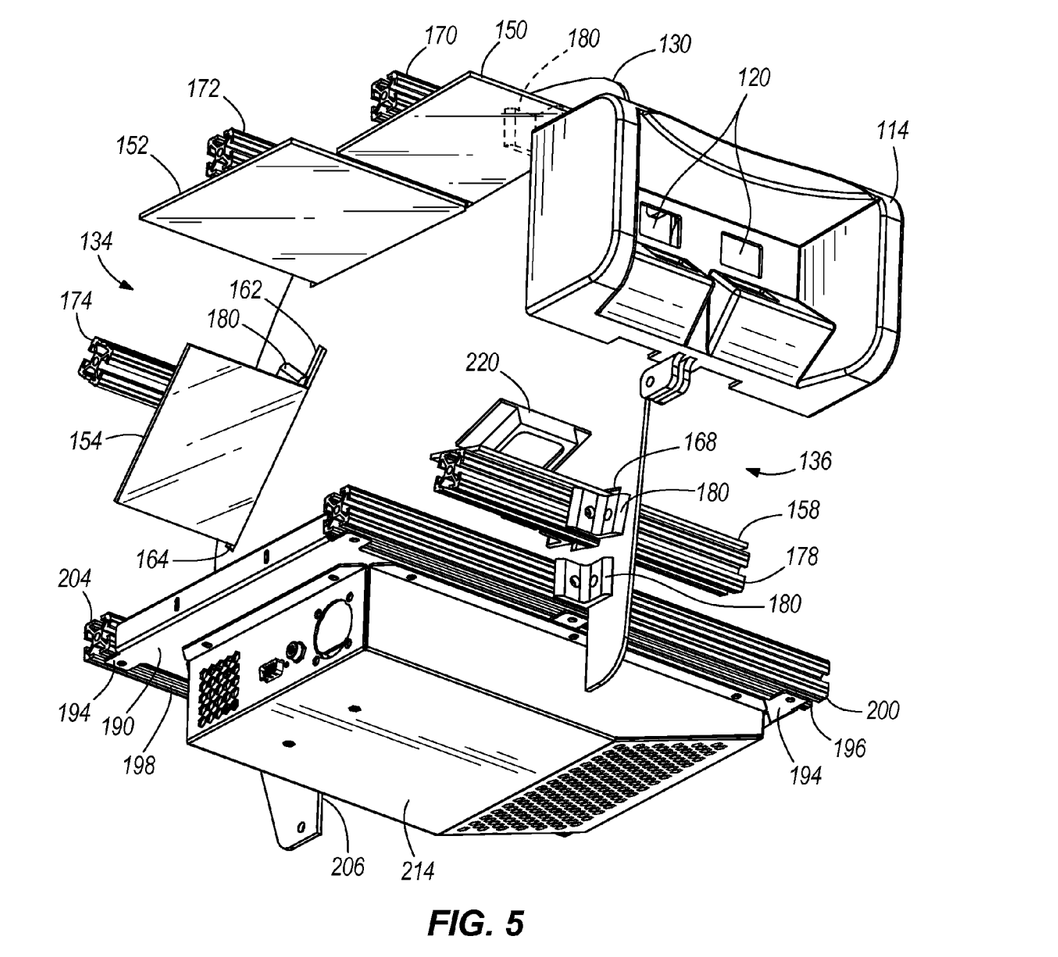
FIG. 5 is a third internal perspective view of the vision tester of FIG. 1.

Referring to FIGS. 3-5, the internal components of the tester 100 are shown. A partition 130 separates a left side 134 from a right side 136 and generally extends from a bottom to a top of the tester 100. Individual mirrors 150, 152, 154, 156, 158 extend from the left side 134 to the right side 136 through slots 160, 162, 164, 166, 168 in the partition 130 specifically sized to receive the respective mirrors 150, 152, 154, 156, 158. Each mirror 150, 152, 154, 156, 158 is coupled to a channel bracket 170, 172, 174, 176, 178, and each channel bracket is coupled to the partition 130 through opposing angle brackets 180, as will be further detailed below.

An electronic mounting bracket 190 presents outwardly projecting tabs 194 (FIG. 5) that couple to the undersides 196, 198 of two channel brackets 200, 204 extending through a bottom aperture 206 in the partition 130. The channel brackets 200, 204 are affixed to the partition 130 through additional angle brackets 180. A flat panel monitor 210 for displaying images is secured within the electronic mounting bracket 190. In other constructions, the flat panel monitor 210 may be another electronic device having a computer or other video screen operable to project images. An enclosure shield 214 is coupled to the bottom of the mounting bracket 190 and contains electronic components and hardware commonly associated with at least partial operation of the flat panel monitor 210. The flat panel monitor 210 is specifically configured, through software or other means, to project two images, one for each eye, on either side of the partition 130 for vision testing, i.e., an image is presented on the left side 134 and another image, for example a separate image, or a slightly offset image, is presented on the right side 136. A magnifier 220 (shown on the left side 134) adjusts a projected image for the near field lens set 124, as will be further detailed below. It should be noted that while the illustrated constructions include a single flat panel monitor 210 as the sole image producing device, other constructions could employ two separate monitors with one monitor producing a left image and a second monitor producing a right image. In still other constructions more than two monitors could be employed with the different monitors producing images that simulate different views. For example, two monitors could be positioned to produce near field images with two additional monitors being used to produce far field views. No matter the number of monitors employed, the one or more monitors collectively make up an image projecting system, with other systems for projecting images being possible. It should also be noted that in order to test both near field and far field vision, the vision testing system provides two separate optics paths. While both paths are about the same length (e.g., about 3.5 feet) each optical path is arranged to simulate a different distance. For near field vision, the optics adjust the image so that the test subject perceives the image as being about 16 inches (i.e., less than half the actual optical distance) from the test subject's eyes. For far field vision, the optics are arranged in a reverse telescope design so that the test subject perceives the image as being about 20 feet (i.e., more than five times the actual optical distance) from the test subject's eyes.

Figure 6:
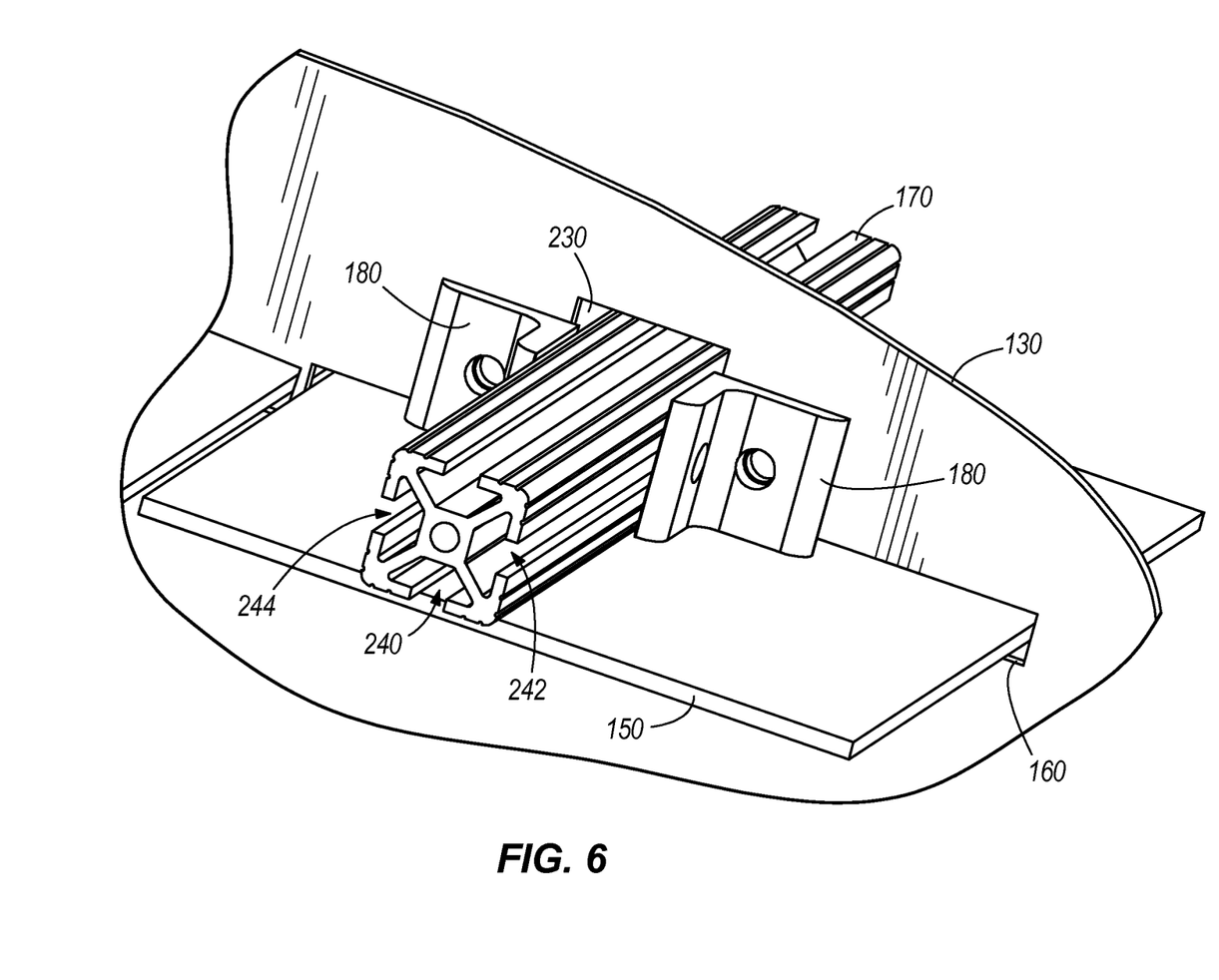
FIG. 6 is a partial perspective view of a mirror coupled to the partition of the vision tester of FIG. 1.

FIG. 6 illustrates the configuration of a mirror (e.g., mirror 150) and a channel bracket (e.g., channel bracket 170) with the partition 130. As shown, the channel bracket 170 extends through an aperture 230 in the partition 130 sized to accommodate the cross sectional area of the channel bracket 170. The aperture 230 is approximately centered with respect to the slot 160 such that the bracket 170 is removably fixed to the mirror 150 at an approximate mirror midpoint. The channel bracket 170, conventionally known in the art, includes a pin connector (not shown) that is disposed within a first channel 240 of the channel bracket 170 and coupled to the mirror 150. Second pins (not shown) within second and third channels 242, 244 attach to the angle brackets 180 affixed to the partition 130, holding the mirror 150 in position. The mirrors 152, 154, 156, 158 and respective channel brackets 172, 174, 176, 178 are similarly configured with the partition 130. Thus, each mirror 150, 152, 154, 156, 158 is exclusively supported by an individual channel bracket 170, 172, 174, 176, 178 and is therefore concurrently alignable on the left side 134 and the right side 136, i.e., visual alignment of both sides 134, 136 of the tester 100 is accomplished simultaneously. In addition, individually supporting the mirrors 150, 152, 154, 156, 158 through the brackets 170, 172, 174, 176, 178 eliminates external torques on the mirrors, reducing their susceptibility to breakage.

Figure 7:
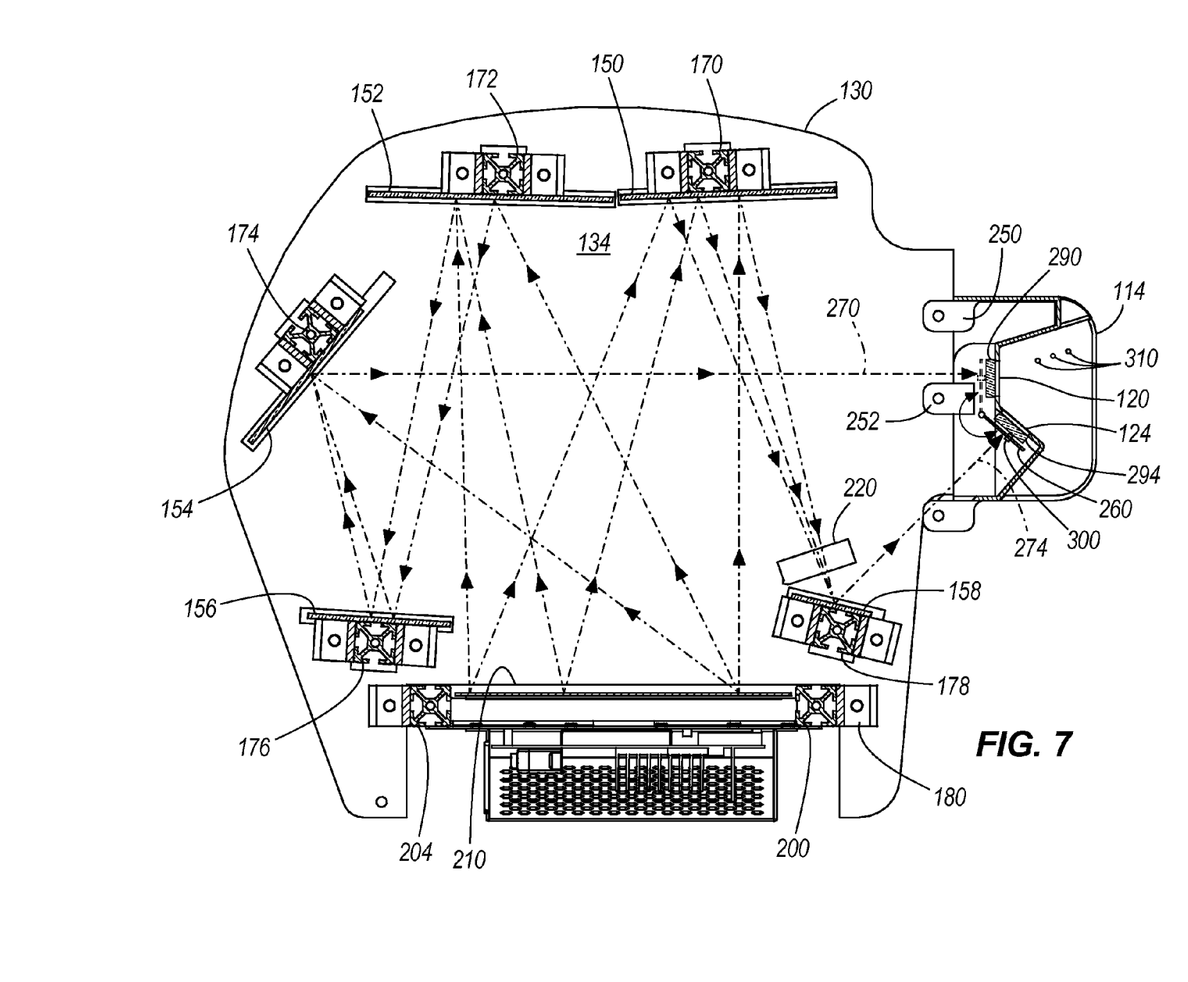
FIG. 7 is a cross sectional view of the vision tester taken along line 7-7 of FIG. 2.

FIG. 7 shows a cross section through the left side 134 of the tester 100. The optics head 114 is fastened to the partition 130 through two opposing tab supports 250, 252 that are preferably integrally-formed as one piece with the optics head 114. A two-position opaque cover 260 coupled to the optics head 114 and rotates between a first position that blocks the line of sight 270 of the far field lens set 120 and a second position that blocks the line of sight 274 of the near field lens set 124. A first prism 290 is optically coupled to the far field lens set 120 along the line of sight 270, and a second prism 294 is optically coupled to the near field lens set 124 along the line of sight 274. The prisms 290, 294 receive the images reflected from the mirrors 150, 152, 154, 156, 158 and shift those images, e.g., inward, to improve what is perceived by the viewer. In the illustrated construction, the prisms 290 of the far field lens set 120 are arranged such that the right side prism 290 shifts the image toward the left and the left side prism 290 shifts the image to the right. The near field prisms 294 shift the images in a similar direction with only the extent of the shift being different. The shift in the position of the images produced by the prisms 290, 294 assures that the images are properly aligned at the desired perceived distance during viewing.

In some constructions, LEDs 300 or other light emitting devices are positioned on the cover 260, as illustrated in FIG. 7. When the cover 260 is in a first position, the test subject will be looking through the opposite openings, thereby placing the cover LEDs 300 in the test subject's vertical peripheral vision. Thus, by activating one or more of the cover LEDs 300, the device is able to test a test subject's vertical peripheral vision (either above or below depending on the position of the cover 260). In the past, it was difficult to test vertical peripheral vision due to the placement of lenses or other optical instruments. The addition of the cover 260 and more importantly, the LEDs 300 on the cover, enables the tester 100 to test vertical peripheral vision of the test subject.

Referring again to FIG. 7, in operation an image is projected from the flat panel monitor 210. The image is generally first reflected from mirrors 150 and 152. The reflected image from mirror 150 is directed through the magnifier 220 to the mirror 158, which is angled such that the final image presented to the user is observable and within the line of sight 274 of the near field lens set 124. The reflected image from mirror 152 is directed to the mirror 156. The mirror 156 is angled to reflect that image to the mirror 154. The resulting image reflected from mirror 154 is observable and within the line of sight 270 of the far field lens set 120. As illustrated, the location of the support brackets 170, 172, 174, 176, 178 outside of the area of reflection created by the mirrors 150, 152, 154, 156, 158 eliminates visual obstructions to any of the reflected images.

Another image is concurrently projected from the flat panel monitor 210, as previously described, and identically reflected on the right side 136 of the tester 100. In this manner, the user experiences a left side image and a right side image independently to the left eye and the right eye via lens sets 120, 124.

During near field testing, the cover 260 is rotated over the far field lens set 120 such that the far field line of sight 270 is obstructed. Thus, the user observes an image through the near field lens set 124 and communicates what is seen to the operator. During far field testing, the cover 260 is rotated over the near field lens set 124 such that the near field line of sight 274 is obstructed. The user observes an image through the far field lens set 120 and again communicates what is perceived to the operator for evaluation.

More than one image, or more than one type of image, can be shown sequentially to the user, depending on the specific testing to be performed. As an example, the tester 100 with the flat panel monitor 210 can be configured to show more images than currently used with conventional testing equipment. This renders it more difficult for a user to cheat on the vision test, for instance, by memorizing a set number of images and recording or reciting them to the operator without regard to the actual images shown. In some constructions, the entire test can be computerized, to include user response inputs, such that an operator need not be present during the test.

As illustrated in FIG. 7, peripheral vision assessment is integrated with the vision testing system for supplemental vision testing. Additional reflecting mirrors, video screens, or, as illustrated in FIG. 7 lighting components such as LEDs 310 (see FIG. 7), positioned on the right side 134 and the left side 136 can be optionally activated during assessment to evaluate a user's response to side peripheral images or stimuli. The additional mirrors, video screens, or lighting components can, for example, be accommodated within side housings fixedly or removably attached to a modified outer hood 110. As discussed, vertical peripheral vision is tested using the LED 300 located in the cover 260.

Figure 8:
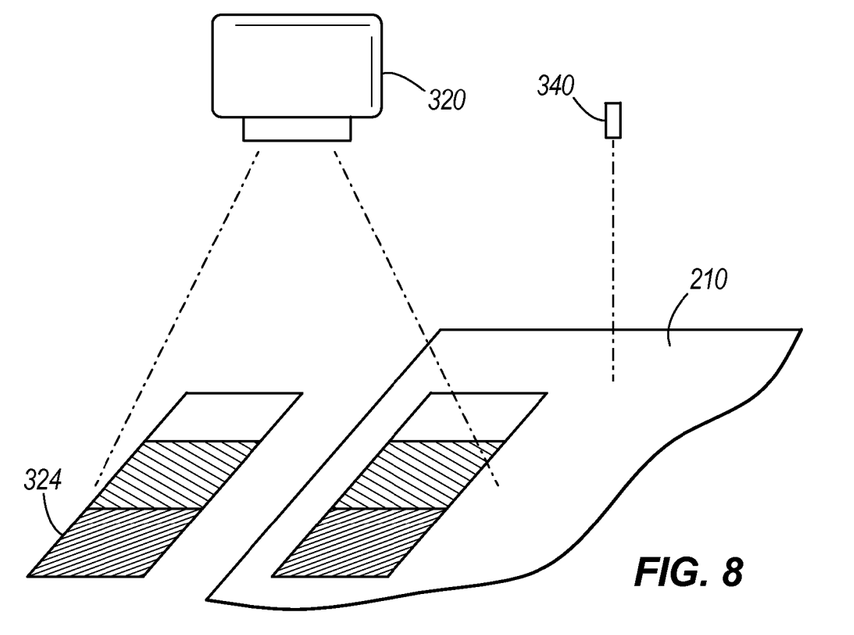
FIG. 8 is a schematic illustration of a calibration system for the vision tester of FIG. 1.

FIG. 8 schematically illustrates an arrangement for calibrating both the color and the brightness of the flat panel monitor 210. Each time the flat panel monitor 210 is activated it must be properly calibrated in order for any tests to be valid. A color sensor such as a camera or a CCD detector 320 is positioned to simultaneously view a portion of the flat panel monitor 210 as well as a standard color card 324 positioned adjacent an edge of the flat panel monitor 210. The camera 320 simultaneously images both the flat panel monitor 210 and the standard color card 324 and adjusts the monitor color settings until the colors of the monitor 210 match those of the color card 324. In preferred arrangements, a closed loop computer control uses a computer 330 to adjust the color settings of the flat panel display 210. The term "computer" as used herein should be interpreted broadly to include desktop or lap top computers, tablets, smart phones, and any other device capable of receiving, sending, storing or manipulating data in electronic form.

With continued reference to FIG. 8, the vision tester 100 also includes a brightness calibration system. The brightness calibration system includes a light sensor 340 such as a camera or CCD sensor that is positioned to detect an image from the flat panel monitor 210. During start-up a standard image is displayed and the light sensor 340 measures the light level displayed. A second closed loop control system utilizes the computer 330 to adjust the brightness of the monitor 210 until the light level measured by the light sensor 340 equals a predetermined setting.

The present invention has been described as it would be used for near field and far field vision testing. However, the device is well-suited to performing a full range of vision testing. In addition, the system 100 is capable of performing the tests, compiling the results, comparing those results to a standard, and outputting the results electronically (e.g., via email, computer, tablet, etc.) or via a printer or other output device autonomously.

In one arrangement, the device is capable of performing at least the following vision tests:

Stereopsis—Test the ability to judge depth or the relative distance of objects in space and to orient one's position in relation to them. Binocular vision is essential to this ability. Also called Depth Perception. Depth perception is to be recorded in Seconds of Arc or Shepard-Frye Percentage Phoria—the relative direction of the eyes during binocular fixation on a given object in the absence of an adequate fusion stimulus, i.e., a misalignment of the eyes when fixation on a single object is broken and the eyes are no longer looking at the same object. Tests latent deviation of the eyes. The misalignment can be lateral or vertical or both. A scale of prism diopters indicates the measure of imbalance.

Day and Night Test: Vision tests (usually Acuity or Contrast Sensitivity Tests) performed at day or night illumination levels to determine the visual result in real world conditions Contrast Sensitivity: Tests the ability to detect luminance contrast. In psychophysical terms it is the reciprocal of the minimum perceptible contrast. The measurement of the contrast sensitivity of the eye is a more complete assessment of vision than standard visual acuity measurement. It provides an evaluation of the detection of objects (usually sinusoidal gratings or letters) of varying spatial frequencies and of variable contrast and thus obtaining a contrast sensitivity function.

Color Vision Test: Tests the test subject's ability to determine perception of the different colors making up the spectrum of visible light. Test targets can include but not limited to; Ishihara, E's and color plates.

Peripheral Vision Test: Tests part of vision that occurs outside the very centre of gaze both horizontally and laterally. There is a broad set of non-central points in the field of view that is included in the notion of peripheral vision. The test subject responds at various distances from their central vision. The measurement is in degrees.

Fusion Testing Test: Tests the ability of the eyes to coordinate two separate images of the same object in the two eyes into one. The test results are either pass or fail.

Glare Testing Test: A test to measure a test subject's ability to maintain the spatial resolution of the visual processing system from off axis, (non-targeted), bright light, i.e., on a very bright sunny day and/or at night with the presence of automobile headlights.

Glare Recovery Test Tests: the time of the test subject's retina to recover to their normal visual acuity after being exposed to very bright retina bleaching light.

Acuity (Day and Night)—Is a measure of the spatial resolution of the visual processing system. VA is tested by requiring the person whose vision is being tested to identify characters i.e., letters, numbers or symbols to mention a few on a chart from a set distance. The Chart characters are represented as black symbols against a white background (for maximum contrast). The distance between the person's eyes and the testing chart is set at a sufficient distance to approximate near, far or intermediate. Results may be recorded in Snellen Notation, Metric, Decimal, LogMAR, Cycles per Degree, Jeagar to name a few. The test may be administered either Monocularly, or Binocularly.

By using computer generated images, all of the aforementioned tests can be presented in the standard method of multiple targets during testing. A new method that can be utilized in this instrument allows the optotype to be presented one at a time using a thresholding methodology to save testing time and make test subject confusion less of a problem.

Figure 9:
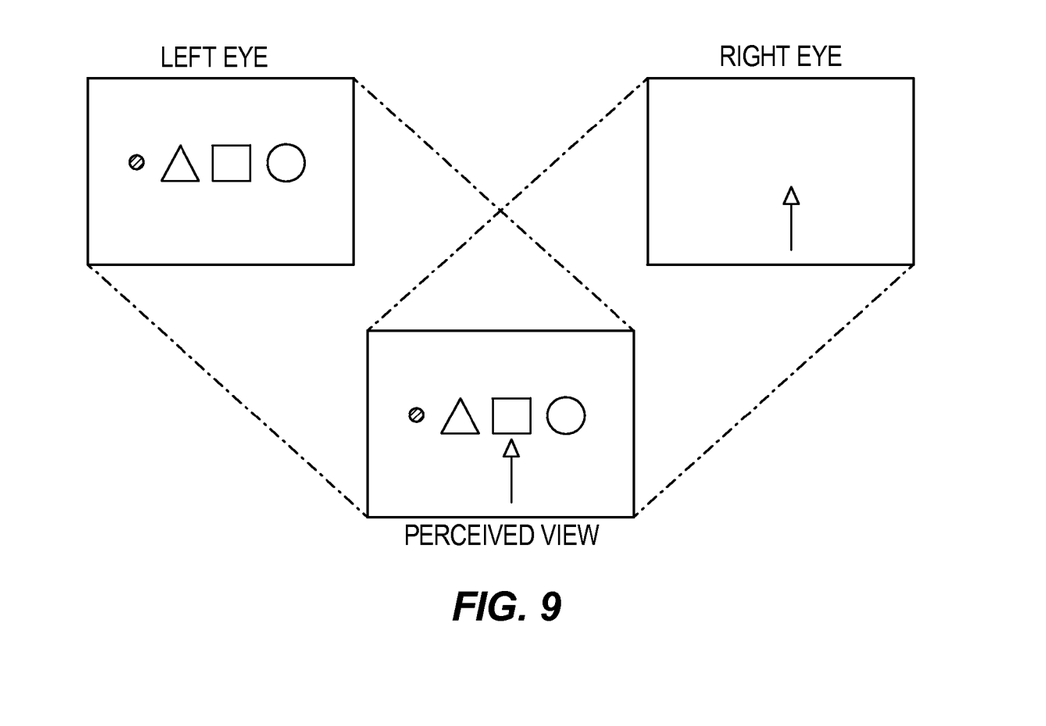
FIG. 9 is an illustration of a left eye image, a right eye image, and a perceived image based on the left eye image and the right eye image.

As required, the vision tester 100 is capable of performing at least some of the above-named tests simulating near, far, and intermediate distances for each of the above. As described, several of the above-identified tests use identical but offset images presented on the monitor 210 and displayed to a user via a desired set of optics (mirrors, lenses, prisms, etc.) to simulate the desired three dimensional image at a preferred distance (e.g., near, far, intermediate). However, some of the tests identified above use two different images with each image presented on only one side of the monitor. For example, as illustrated in FIG. 9, a particular test may present an image including a series of shapes on one side with an arrow on the other side. When both eyes of the test subject see the two images, they are combined by the subject's brain into a single perceived three dimensional image with the arrow pointing at one of the particular shapes in the series. The test subject then identifies that object. The object identified by the test subject is indicative of the alignment of the vision fields produced by the test subject's two eyes.

Figure 10:
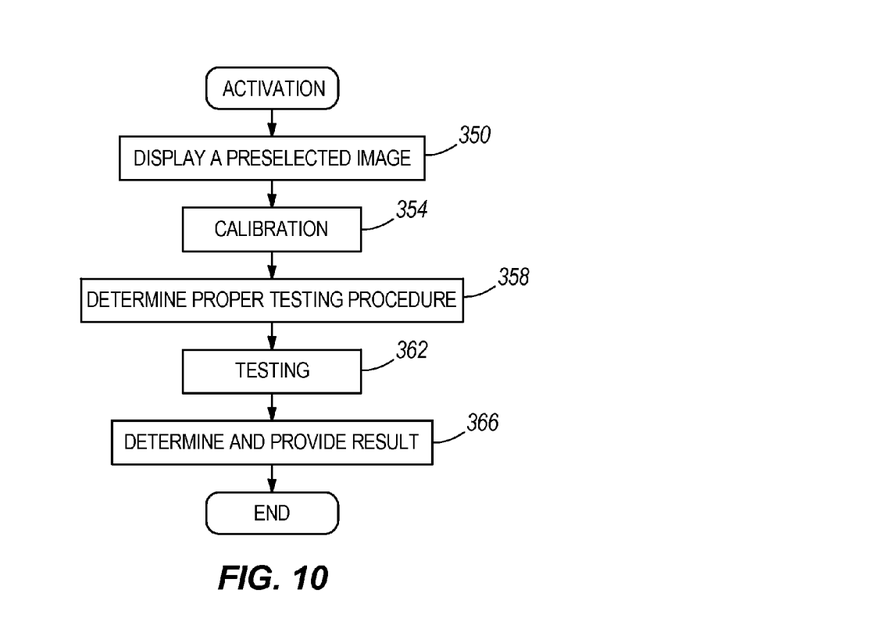
FIG. 10 is a flow diagram of the vision testing procedure.
Figure 11:
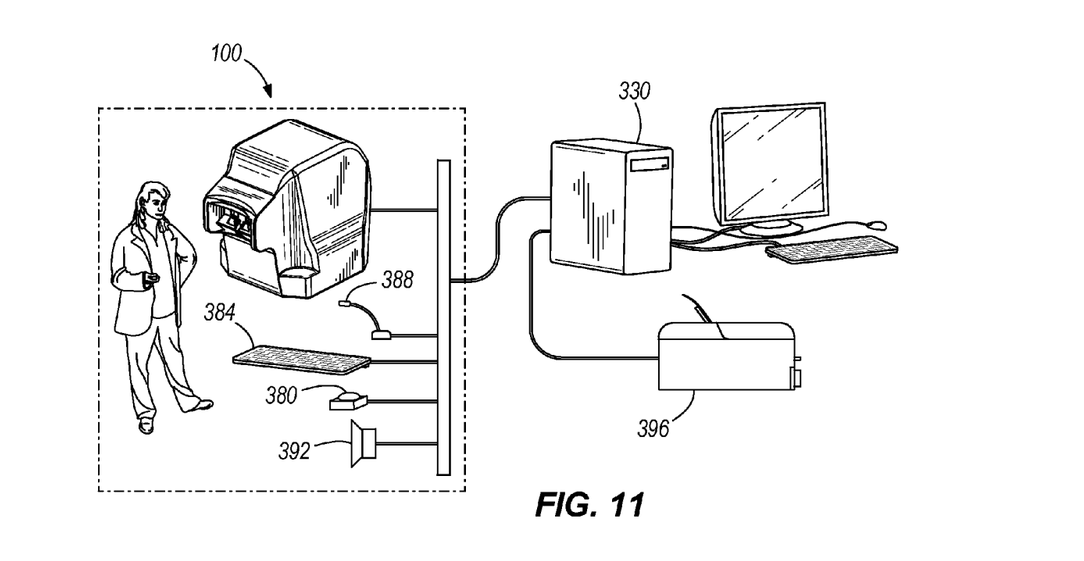
FIG. 11 is a schematic drawing of a vision testing system.

Referring to FIGS. 10 and 11, in use, a test subject or an operator activates the vision tester 100. The monitor 210 activates and displays a preselected start-up image (step 350) such as a white screen with a number of color samples positioned adjacent the color card 324 (see FIG. 8). The computer 330 calibrates the color of the flat panel monitor 210 as well as the brightness (step 354) before proceeding with the vision testing. Once the monitor 210 is calibrated, the testing of the test subject can begin. In a preferred arrangement, the computer 330 includes a database that contains a plurality of possible vision tests that can be performed along with various standards that may depend on things such as the occupation of the test subject or the age of the test subject. For example, a first test subject may be a pilot candidate who must pass seven or more different vision assessments while a second test subject may be a welder who must pass only three particular vision tests. Once the particular battery of tests and the testing procedure is determined (step 358), the testing begins (step 362). As illustrated in FIG. 11, the vision testing system may include manual input members such as buttons, dials, or switches 380, or a keyboard 384, or preferably includes voice recognition that allows the test subject to state answers through a microphone 388 to questions asked during the testing. During the test, a test operator, or preferably the computer 330 of the vision testing system itself, asks the test subject questions through a speaker 392 about the images being presented, and the test subject answers those questions. The answers are recorded by the computer 330 and compared against the correct answers to determine a test result. The test result is then compared to a standard saved in the database for the particular test subject to determine if the test subject passes or fails the particular test (step 366). Upon completion, an electronic test result (e.g., text, email, or image) is presented to the test subject and/or the test operator. Alternatively, the vision testing system 100 is coupled to a printer 396 or other output device that provides for a physical output of the test results.

The inclusion of a computer 330 and monitor 210 in the tester 100 provides several additional advantages. For example, in some constructions, an operator can use a mouse or other input device to point to specific optotypes, images, or regions to help instruct the patient and speed or improve testing.

Various features and advantages of the invention are set forth in the following claims.

What is claimed is:

1. A vision testing device comprising:
  a partition defining a first side and a second side;

an electronic device operable to project a first image to the first side and a second image to the second side, the first image and the second image comprising computer-generated images, wherein the first image is identical to but offset from the second image;

a mirror extending from the first side to the second side and positioned to reflect the first image and the second image;

a first viewing lens in optical communication with the first side and configured to receive the first image reflected from the mirror; and a second viewing lens in optical communication with the second side and configured to receive the second image reflected from the mirror.

2. The vision testing device of claim 1, wherein the mirror extending from the first side to the second side is a first mirror, the vision testing device further including a second mirror extending from the first side to the second side and positioned to reflect the first image from the first mirror and the second image from the first mirror.

3. The vision testing device of claim 2, wherein the first viewing lens is configured to receive the first image reflected from the second mirror and the second viewing lens is configured to receive the second image reflected from the second mirror.

4. The vision testing device of claim 2, further including a third mirror extending from the first side to the second side and positioned to reflect the first image from the second mirror and the second image from the second mirror.

5. The vision testing device of claim 4, wherein the first viewing lens is configured to receive the first image reflected from the third mirror and the second viewing lens is configured to receive the second image reflected from the third mirror.

6. The vision testing device of claim 1, wherein the first viewing lens and the second viewing lens comprise a far field lens set for evaluating a far field vision.

7. The vision testing device of claim 1, wherein the electronic device includes a flat panel monitor.

8. A vision testing device comprising:
a partition defining a first side and a second side;
an electronic device operable to project a first image to the first side and a second image to the second side, the first image and the second image comprising computer-generated images, wherein the first image is identical to but offset from the second image;
a mirror extending from the first side to the second side and positioned to reflect the first image and the second image;
a first viewing lens in optical communication with the first side and configured to receive the first image reflected from the mirror;
a second viewing lens in optical communication with the second side and configured to receive the second image reflected from the mirror, wherein the mirror extending from the first side to the second side is a first mirror, the vision testing device further including a second mirror extending from the first side to the second side and positioned to reflect the first image from the first mirror and the second image from the first mirror: and
a third viewing lens in optical communication with the first side and configured to receive the first image reflected from the second mirror and a fourth viewing lens in optical communication with the second side and configured to receive the second image reflected from the second mirror.

9. The vision testing device of claim 8, wherein the third viewing lens and the fourth viewing lens comprise a near field lens set for evaluating near field vision.

10. A vision testing device comprising:
a partition defining a first side and a second side;
an electronic device operable to project a first image to the first side and a second image to the second side, the first image and the second image comprising computer-generated images;
a first viewing lens configured to receive the projected first image; and
a second viewing lens configured to receive the projected second image.

11. The vision testing device of claim 10, further including a mirror extending from the first side to the second side and positioned to reflect the first image and the second image.

12. The vision testing device of claim 11, wherein the first viewing lens is configured to receive the first image reflected from the mirror and the second viewing lens is configured to receive the second image reflected from the mirror.

13. The vision testing device of claim 11, wherein the partition defines an aperture, and wherein the mirror extends through the aperture.

14. The vision testing device of claim 13, further comprising an individual bracket coupled to the partition, wherein the mirror is coupled to the individual bracket.

15. The vision testing device of claim 14, wherein the mirror is coupled to the individual bracket at an approximate midpoint of the mirror.

16. The vision testing device of claim 10, wherein the first viewing lens and the second viewing lens comprise a far field lens set for evaluating a far field vision.

17. A vision testing device comprising:
a partition defining a first side and a second side;
an electronic device operable to project a first image to the first side and a second image to the second side, the first image and the second image comprising computer-generated images;
a first viewing lens configured to receive the projected first image;
a second viewing lens configured to receive the projected second image, wherein the first viewing lens and the second viewing lens comprise a far field lens set for evaluating a far field vision; and
a third viewing lens configured to receive the first image and a fourth viewing lens configured to receive the second image, and wherein the third and fourth viewing lenses comprise a near field lens set for evaluating near field vision.

18. The vision testing device of claim 17, further including a magnifier in a line of sight of the near field lens.

19. The vision testing device of claim 18, further including a cover rotatable between a first position that blocks a line of sight of the far field lens set and a second position that blocks the line of sight of the near field lens set.

20. A vision testing device comprising:
an outer hood enclosing an internal space, the internal space including
an electronic device operable to project a computer-generated first image and a computer-generated second image, the second image offset from the first image, and
a partition disposed to separate the first image from the second image; and
a viewing member coupled to the outer hood for providing viewing access to the internal space, the viewing member including a first viewing lens configured to receive the first image, and a second viewing lens configured to receive the second image.

21. A method of testing the vision of a test subject using a single vision testing apparatus, the method comprising:

providing a subject viewing space including a first pair of view windows and a second pair of view windows;

projecting a first image using an image projecting system, the first image arranged to be viewed by the left eye of the test subject;

projecting a second image using the image projecting system, the second image arranged to be viewed by the right eye of the test subject, the second image being at least one of different than the first image and identical but offset from the first image;

separating the first image and the second image such that the first image is not viewable by the right eye at the same time that the second image is viewed by the left eye;

collecting an input from the test subject, the input based on the test subject's perception during the simultaneous viewing of the first image and the second image;

determining a result based at least in part on the input, the result being indicative of the quality of one aspect of the test subject's vision; and comparing the result to a database of result standards to determine if the test subject's vision with regard to the particular one aspect exceeds the result standard.

22. A vision testing system autonomously operable to evaluate the vision of a plurality of different test subjects having different backgrounds, the vision testing system comprising:

a computer including a database of vision tests, each vision test having a pass/fail criteria based at least in part on the background of the test subject;

a monitor coupled to the computer and operable in response to the computer to display a left side image and a right side image;

a divider positioned to separate the left side image and the right side image;

a first viewing station including a first viewing port arranged to selectively provide a view of the left side image and the right side image and a second viewing port arranged to selectively provide a view of the left side image and the right side image;

a first optics path positioned to direct the left side image and the right side image to the first viewing port, the first optics path arranged to simulate a near field view of the left side image and the right side image; and a second optics path different than the first optics positioned to direct the left side image and the right side image to the second viewing port, the second optics path arranged to simulate a far field view of the left side image and the right side image.

23. The vision testing system of claim 22, wherein the second optics path is arranged in a reverse binocular arrangement such that the apparent distance between the test subject and the left side image and the right side image is at least five times the actual distance between the test subject and the left side image and the right side image.

24. The vision testing system of claim 22, wherein the first optics path is arranged such that the apparent distance between the test subject and the left side image and the right side image is less than half the actual distance between the test subject and the left side image and the right side image.

25. The vision testing system of claim 22, wherein the first viewing station includes a first left eye opening and a first right eye opening.

26. The vision testing system of claim 25, further comprising a first left prism arranged to shift the left side image and a first right prism arranged to shift the right side image.

27. The vision testing system of claim 22, wherein the second viewing station includes a second left eye opening and a second right eye opening.

28. The vision testing system of claim 27, further comprising a second left prism arranged to shift the left side image and a second right prism arranged to shift the right side image.

29. The vision testing system of claim 22, further comprising a cover coupled to the first viewing station and movable between a first position that blocks the first optics path and a second position that blocks the second optics path.

30. The vision testing system of claim 29, further comprising a first light source supported by the cover and selectively activatable to test the vertical peripheral vision of the test subject.

31. The vision testing system of claim 30, further comprising a second light source coupled to the first viewing station and positioned on one side of the first viewing port to test the side peripheral vision of the test subject.

32. The vision testing system of claim 31, wherein the first light source includes a first LED and the second light source includes a second LED.

33. A vision testing system operable to perform a plurality of optical tests, the vision testing system comprising:

a video image producing device operable to produce a left side image and a right side image;

a mechanical divider positioned to separate the left side image and the right side image;

a first optics path positioned to direct the left side image and the right side image to the first viewing port, the first optics path arranged to simulate a near field view of the left side image and the right side image;

a second optics path different than the first optics path and arranged to simulate a far field view of the left side image and the right side image; and a computer operable to select an optical standard to be tested against from a plurality of stored standards, the computer also operable to select the right side image and the left side image based on the optical test being performed and the standard being tested and to compare the test results to the selected standard for the selected optical test to determine if the test subject passes or fails the test.

* * * * *